United States Patent [19]

Whitten et al.

[11] Patent Number: 4,704,396

[45] Date of Patent: Nov. 3, 1987

[54] PHENACYL ESTERS OF 1-SUBSTITUTED-6-(SUBSTITUTED AND UNSUBSTITUTED) DIHYDROLYSERGIC ACIDS USEFUL AS 5HT RECEPTOR ANTAGONISTS

[75] Inventors: Kathleen R. Whitten, Zionsville; William L. Garbrecht, Indianapolis, both of Ind.

[73] Assignee: Eli Lilly and Company, Indianapolis, Ind.

[21] Appl. No.: 811,206

[22] Filed: Dec. 20, 1985

[51] Int. Cl.$^4$ .................... A61K 31/48; C07D 457/04
[52] U.S. Cl. ........................... 514/288; 546/67; 546/68; 546/69
[58] Field of Search ............... 546/69, 67, 68; 514/288

[56] References Cited

U.S. PATENT DOCUMENTS

| | | | |
|---|---|---|---|
| 3,113,133 | 12/1963 | Hofmann et al. | 546/49 |
| 3,183,234 | 5/1965 | Garbrecht | 546/69 |
| 3,228,941 | 1/1966 | Barnardi et al. | 546/69 |
| 3,249,617 | 5/1966 | Hofmann et al. | 546/69 |
| 3,580,916 | 5/1971 | Garbrecht | 546/69 |
| 4,230,859 | 10/1980 | Rucman | 546/69 |
| 4,321,381 | 3/1982 | Mantegani et al. | 546/67 |

FOREIGN PATENT DOCUMENTS 122044 10/1984 European Pat. Off. .

OTHER PUBLICATIONS

Cohen et al, Journal of Pharmacology and Experimental Therapeutics, vol. 227, No. 21, pp. 327–332.
Cohen et al, Journal of Pharmacology and Experimental Therapeutics, vol. 232, No. 3, pp. 770–774.
Lemberger et al, Life Sciences; vol. 35, pp. 71–77.
Cohen et al, Drug Development Research 5:313–321 (1985).
Hingtgen et al, Abstracts, Society for Neuroscience 13th Annual Meeting, Nov. 6–11, 1983, p. 125.

*Primary Examiner*—Donald G. Daus
*Assistant Examiner*—Cecilia Shen
*Attorney, Agent, or Firm*—Bruce J. Barclay; Leroy Whitaker

[57] ABSTRACT

Phenacyl or substituted phenacyl esters of 1-substituted-6-$C_{1-4}$ straight chain alkyl (or allyl)ergoline-8$\beta$-carboxylic acid, useful as 5HT receptor antagonists.

18 Claims, No Drawings

PHENACYL ESTERS OF 1-SUBSTITUTED-6-(SUBSTITUTED AND UNSUBSTITUTED) DIHYDROLYSERGIC ACIDS USEFUL AS 5HT RECEPTOR ANTAGONISTS

BACKGROUND OF THE INVENTION

Garbrecht, U.S. Pat. No. 3,580,916, discloses a group of lysergic (I) and 9,10-dihydrolysergic acid (II) esters formed with various open chain and cyclic diols. The following structures summarize the disclosure in Garbrecht.

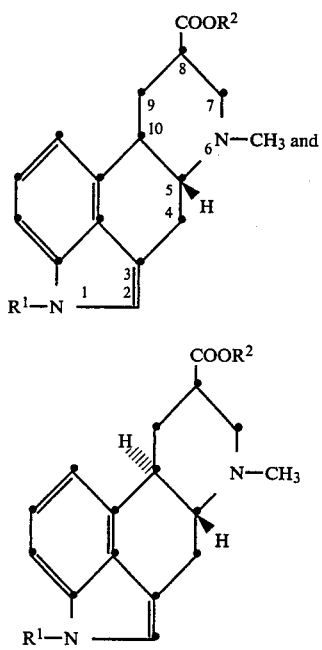

wherein $R^1$ is H, $C_{1-3}$ alkyl, allyl or benzyl and $R^2$ is $C_2$-$C_8$ monohydroxyalkyl, $C_{2-8}$ dihydroxyalkyl or $C_{5-11}$ monohydroxycycloalkyl having from 5-8 ring carbons. The compounds are useful as serotonin antagonists, the patent stating that "In animals, the compounds act as neurosedatives . . . and are therefore useful in calming . . . animals". The use of compounds according to II, wherein $R^2$ is mono or dihydroxyalkyl, in migraine and other disease states characterized by an excess of peripheral 5HT, is disclosed in EPO 122,044 published 10-17-84.

The interest in the Garbrecht compounds has been intensified by the finding that they had excellent peripheral serotonin antagonist activity against $5HT_2$ receptors and did not interact, either as agonists or antagonists, with other receptors, particularly alpha$_1$ receptors.

The most active peripheral serotonin antagonist from Garbrecht was the compound 1-isopropyl-6-methyl-8β(1-methyl-2-hydroxy)propoxycarbonyl-5R-ergoline (II in which $R^1$ is isopropyl and $R^2$ is 1-methyl-2-hydroxypropyl). In the above name, 5R refers to the beta orientation of the C-5 hydrogen. The C-10 hydrogen is alpha—10R, and the beta orientation at C-8 is the same as in either lysergic or 9,10-dihydrolysergic acid—8R. Both of these acids have a 6-methyl group. An alternate name for the Garbrecht compound is 1-isopropyl-9,10-dihydrolysergic acid 1-methyl-2-hydroxypropyl ester. Cohen et al. *J.P.E.T.*, 227, 327 (1983) (Cohen I) reported that the above compound, given the code number LY53857, was a potent antagonist of vascular contraction to serotonin, which effect is mediated by $5HT_2$ receptors. The compound had minimal affinity for vascular alpha adrenergic, dopaminergic and histaminergic receptors ($K_{dissoc.} \cong 10^{-10}$ vs $\cong 10^{-5}$). Other papers on the pharmacology of LY53857 include Cohen et al., *J.P.E.T.*, 232, 770 (1985) (Cohen III), Harriet Lemberger et al., *Life Sciences*, 35, 71 (1984), Cohen, *Drug Development Res.*, 5, 313 (1985), (Cohen IV). Cohen and Fuller, EPO 122,044 published 10-17-84, covers the use of hydroxyalkyl esters of 1-alkyl 9,10-dihydrolysergic acid as peripheral $5HT_2$ receptor antagonists.

Four additional examples of ergolines with a substituent on the indole nitrogen are: U.S. Pat. No. 3,113,133, Hofmann et al., which discloses and claims esters and amides carrying an indole N substituent such as a lower alkyl or alkenyl group or an aralkyl group. The compounds are said to be useful as serotonin antagonists, in treating inflammatory, arthritic and allergic diseases and in treating carcinoid syndrome.

U.S. Pat. No. 3,249,617, Hofmann et al., which covers (indole) N-alkyl or alkyl lysergic acids, useful as intermediates.

U.S. Pat. No. 3,228,941, Bernardi et al., which discloses and claims a group of (indole) N-methylergolines—amides, hydroxamides and amidines. The compounds are alleged to have oxytoxic, adrenolytic, hypotensive, sedative and antienteraminic action.

U.S. Pat. No. 4,230,859 to Rucman which discloses dihydrolysergic acid carrying various $C_{1-5}$ alkyl groups on the indole nitrogen. The compounds are said to be useful as intermediates.

Finally, ergolines actually used in the treatment of migraine include the amides: ergotamine, methysergide and ergonovine.

None of the above references indicate that a phenacyl ester of an $N^1$-alkylated dihydrolysergic acid would have peripheral serotonin antagonist properties.

SUMMARY OF THE INVENTION

This invention provides ergolines of the formula:

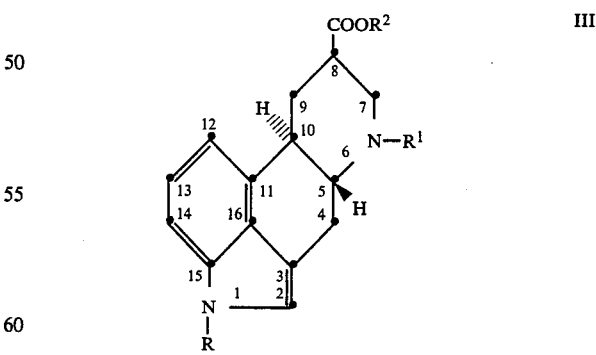

wherein R is primary or secondary $C_{1-8}$ alkyl, $C_{2-4}$ alkenyl—$CH_2$, $C_{3-8}$ cycloalkyl or $C_{3-6}$ cycloalkyl substituted $C_{1-5}$ primary or secondary alkyl, the total number of carbon atoms in R not to exceed 8; $R^1$ is allyl, H or $C_{1-4}$ straight-chain alkyl; ie., methyl, ethyl, n-butyl, or n-propyl, and $R^2$ is

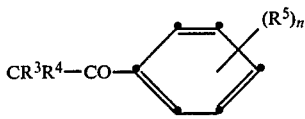

wherein R³ and R⁴ can be individually H, CH₃ or C₂H₅; n is 0, 1 or 2; R⁵ may be OH, OC₁₋₃ alkyl, chloro, bromo, fluoro, CH₃, CF₃ or C₂H₅ when n is 1 or 2; R⁵ may be phenyl when n is 1; and R⁵ may be methylenedioxy when n is 2; and pharmaceutically acceptable acid addition salts thereof. Compounds according to III, wherein R¹ is other than H, are central or peripheral serotonin 5HT₂ receptor antagonists lacking interaction, at 5HT blocking concentrations, with other receptors. Compounds wherein R¹ is H are primarily intermediates.

Groups which R represents include methyl, ethyl, allyl, n-propyl, isopropyl, crotyl, methallyl, n-hexyl, sec-amyl, sec-octyl, n-heptyl, 2,4-dimethylpentyl, 2-ethylpentyl, cyclopropyl, cyclopropylmethyl, cyclopentyl methyl, 2-cyclobutyl ethyl, cyclohexyl, isobutyl, sec.-butyl, 3-methyl-2-butyl, isoamyl, 2-methylhexyl, 3-methylhexyl, 4-methylhexyl(isohexyl), 2-hexyl, 3-hexyl, n-heptyl, 2-heptyl, 3-heptyl, 4-heptyl, n-octyl, 2-octyl, 3-octyl, 4-octyl, isooctyl, 2-methylheptyl, 3-methyl-2-heptyl, and the like. Illustrative of the groups which R² represents include o, m, p-chlorophenacyl, α-methyl-o, m, p-fluorophenacyl, 2,4-dichlorophenacyl, 2,6-dichlorophenacyl, α,α-dimethylphenacyl, 3,4-dimethoxyphenacyl, 2-hydroxyphenacyl, α-methyl-3,4-methylenedioxyphenacyl, 2-phenylphenacyl, o, m, p-methylphenacyl, o, m, p-ethoxyphenacyl, o, m, p-n-propoxyphenacyl and the like.

Compounds according to the above formula are named as ergoline derivatives in which the trans(-) or 5R,10R configuration of the bridgehead hydrogens is specified (The same configuration as in the naturally-occurring 9,10-dihydro ergot alkaloids). In U.S. Pat. No. 3,580,916, a different naming system is used; the basic ring system is named as a 6aR,10aR-4,6,6a,7,8,9,10,10a-octahydroindolo[4,3-f,g]quinoline. Illustratively, by the alternate naming system 9,10-dihydrolysergic acid becomes 6aR,10aR-7-methyl-4,6,6a,7,8,9,10,10a-octahydroindolo[4,3-f,g]quinoline-9β-carboxylic acid. Another equally valid name for 9,10-dihydrolysergic acid is 6-methyl-8β-carboxyergoline. We prefer to use the trivial name "ergoline" with the numbering system specified in III above for compounds in which R¹ is other than methyl and the 9,10-dihydrolysergic acid nomenclature for 6-methyl derivatives (R¹ is methyl).

In addition, in 9,10-dihydrolysergic acid, the C-8 carboxyl is beta or R. Thus, again using the ergoline naming system, derivatives of 9,10-dihydrolysergic acid become derivatives of 5R,8R,10R (or 5β,8β,10α) 6-methylergoline-8β-carboxylic acid.

While the configuration at asymmetric carbons 5,8 and 10 in formula III is set (5β, 8β and 10α), the ester group may contain an additional asymmetric carbon when one of R³ and R⁴ is other than H. For example, α-methylphenacyl alcohol exists as a racemate containing two enantiomers or stereoisomers. Esters prepared from this racemic alcohol will also exist in two diastereoisomeric forms. This invention contemplates the use of all such optically active or racemic esters as peripheral serotonin antagonists.

Pharmaceutically-acceptable acid addition salts of the compounds of formula III include salts derived from non-toxic inorganic acids such as: hydrochloric acid, nitric acid, phosphoric acid, sulfuric acid, hydrobromic acid, hydriodic acid, phosphorous acid and the like, as well as salts derived from non-toxic organic acids such as aliphatic mono and dicarboxylic acids, phenyl-substituted alkanoic acids, hydroxy alkanoic and alkandioic acids, aromatic acids, aliphatic and aromatic sulfonic acids, etc. Such pharamceutically-acceptable salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, fluoride, acetate, propionate, caprylate, acrylate, formate, isobutyrate, caprate, heptanoate, propiolate, oxalate, malonate, succinate, suberate, sebacate, fumarate, maleate, mandelate, butyne-1,4-dioate, hexyne-1,6-dioate, benzoate, chlorobenzoate, methoxybenzoate, phthalate, terephthalate, benzenesulfonate, toluenesulfonate, chlorobenzenesulfonate, xylenesulfonate, phenylacetate, phenylpropionate, phenylbutyrate, citrate, lactate, β-hydroxybutyrate, glycollate, malate, tartrate, methanesulfonate, propanesulfonate, naphthalene-1-sulfonate, naphthalene-2-sulfonate and the like salts.

Illustrative compounds of this invention include:
1-methyl-6-ethyl-8β-(p-methoxyphenacyl)oxycarbonylergoline tartrate
1-n-propyl-6-allyl-8β-(o-bromophenacyl)oxycarbonylergoline sulfate
1-cyclopropylmethyl-6-n-propyl-8β-(m-hydroxyphenacyl)oxycarbonylergoline citrate
α,α-dimethyl-p-methylphenacyl 1-n-octyl-9,10-dihydrolysergate benzoate
α,α-diethyl-p-trifluoromethylphenacyl 1-allyl-9,10-dihydrolysergate phosphate
α-ethyl-m-ethylphenacyl 1-isopropyl-9,10-dihydrolysergate lactate
3,4-methylenedioxyphenacyl 1-isopropyl-9,10-dihydrolysergate succinate
2,4-dichlorophenacyl 1-ethyl-9,10-dihydrolysergate hydrobromide and the like.

The preparation of compounds represented by formula III above follows the general method of U.S. Pat. No. 3,580,916. According to this procedure, dihydrolysergic acid is first alkylated on the indole nitrogen using standard procedures—base plus an aliphatic halide. Liquid ammonia is a convenient solvent with sodamide as the base and an alkyl, cycloalkyl, or cycloalkyl-substituted C₁₋₅ alkyl iodide or an alkenyl chloride or bromide as the alkylating agent. (See also U.S. Pat. No. 3,183,234 Garbrecht and Lin, which contains general directions and a specific example of the above alkylation procedure).

Alternatively, the process described in the copending application of Marzoni, Ser. No. 728,339 filed Oct. 1, 1985, can be used whereby an aryl sulfonate of the formula R—O—SO₂—phenyl—Y, wherein Y is H, Br, NO₂ or CH₃, is used in the presence of an alkali metal hydroxide, conveniently sodium hydroxide, in an aprotic solvent such as DMSO.

With indole nitrogen substituent in place, if 1-R-9,10-dihydrolysergic acid (R¹ is methyl) is the starting material, the next step in the synthetic procedure is esterification. Where the acid and phenacyl alcohol are used, the procedure requires relatively mild reaction conditions according to U.S. Pat. No. 3,580,916. The reaction is, however, an otherwise standard acid-catalyzed esterification. The free acid and the phenacyl alcohol are the reactants and a convenient work-up of the esterification mixture involves partitioning between water and a water-immiscible solvent; $(CH_2Cl)_2$ for example.

Alternatively, and preferably, however, an alkali metal salt of the 1-substituted-9,10-dihydrolysergic acid, conveniently the lithium salt, is reacted with phenacyl bromide or a substituted phenacyl bromide.

If the final product is not a 9,10-dihydrolysergic acid ester (ie; not a 1-R-6-methylergoline-8β-carboxylic acid ester), but is a 6-ethyl, 6-n-propyl, 6-n-butyl, 6-allyl or the like derivative, the removal of the 6-methyl group must take place prior to the final esterification with the phenacyl alcohol or phenacyl halide. In this procedure, we prefer to use a lower alkyl ester of a 1-R-9,10-dihydrolysergic acid as a starting material (ester formed with $R^6OH$ where $R^6$ is methyl or ethyl). Replacement of the 6-methyl group with ethyl, n-propyl, allyl, n-butyl, can be carried out by the procedure of Kornfeld and Bach, U.S. Pat. No. 4,166,182, whereby the 6-methyl group is reacted with cyanogen bromide to form an N-cyano derivative. The cyano group is then removed by hydrogenation using zinc dust and hydrochloric acid or preferably, with base in ethylene glycol or other suitable solvents. This latter procedure yields a product containing a free carboxyl at C-8 since the hydrolysis procedure also saponifies the lower alkyl ester group. Next, reesterification with the desired $R^2OH$ or $R^2Br$ or $R^2Cl$ takes place followed by alkylation or allylation at N-6 using an allyl chloride or alkyl iodide in the presence of base, conveniently in DMF solution.

This procedure is graphically illustrated in Reaction Scheme 1 below.

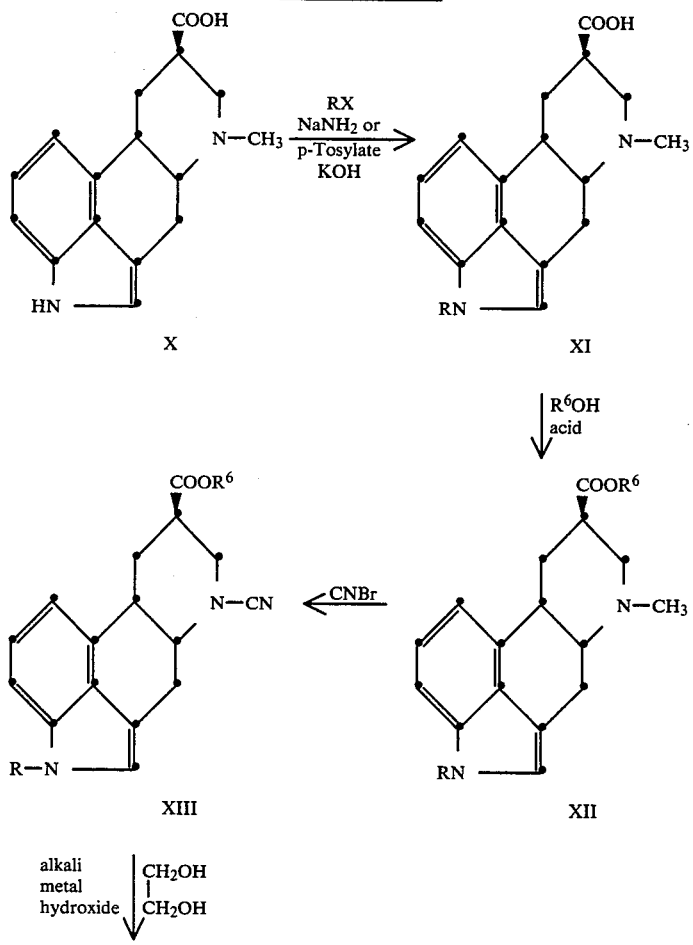

Reaction Scheme 1

Reaction Scheme 1

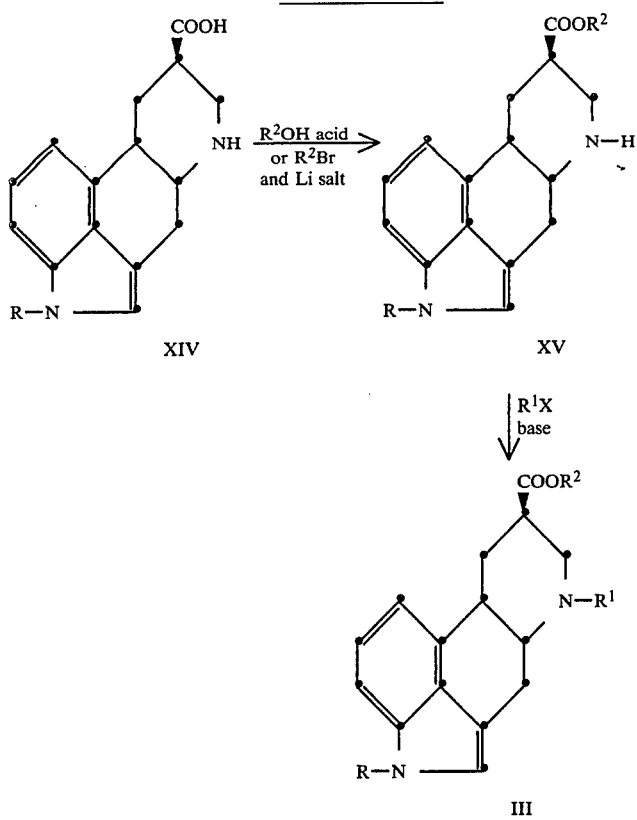

More specifically, in the above Reaction Scheme, 9,10-dihydrolysergic acid (X) may be alkylated on the indole nitrogen with an alkyl ($C_{1-8}$ alkyl) halide a $C_{2-4}$ alkenyl-$CH_2$ halide, a $C_{3-6}$ cycloalkyl halide or a $C_{3-6}$ cycloalkyl-$C_{1-5}$ alkyl halide, (RX), using sodamide to create the reactive anion. Preferably, however, a tosylate (R—O—$SO_2$—tolyl) is employed in the presence of KOH in an aprotic solvent since this latter procedure is more generally applicable than the use of the halide, RX. The product (XI) is then esterified with a lower alkanol $R^6OH$ (a $C_{1-2}$ alkanol preferably) to yield the 1-R alkylated ester (XII). This ester is reacted with CNBr by standard procedures to replace the methyl group with an N-cyano derivative (XIII). Removal of the cyano group under the preferred basic conditions yields a 1-substituted-9,10-dihydro-6-desmethyllysergic acid (XIV), since the basic conditions also saponifies the C-8 lower alkyl ester group. Next, the 1-R-6-desmethyldihydrolysergic acid is re-esterified with a desired phenacyl alcohol or the lithium salt of the acid reacted with the phenacyl halide to yield the 6-desmethyl ester (XV). The piperidine ring nitrogen (N-6) is then realkylated with a $C_{1-4}$ alkyl or allyl halide and base under standard conditions to yield the compounds of this invention (III).

It might seem redundant to realkylate at N-6 with a methyl group since that group is present in the 9,10-dihydrolysergic acid starting material. However, the process would enable one to insert a "tagged" ($C^{14}$ or $H^3$) methyl group for metabolic studies.

Although the above reaction sequence has been illustrated with reference to preparing phenacyl esters, it is apparent that the procedure is readily adaptable to the provision of 1,6-dialkyl ergoline carboxylic acid esters formed with open chain diols, keto alkanols, cycloalkanols, substituted cycloalkanols etc. Such process in all its ramifications is disclosed in the copending application of Whitten et al Ser. No. 782,337 filed Oct. 1, 1985.

The following examples illustrate the preparation of compounds according to III above.

EXAMPLE 1

Preparation of Phenacyl 1-Isopropyl-9,10-dihydrolysergate.

A solution was prepared by dissolving 3.12 g of 9,10-dihydrolysergic acid in 50 ml of methanol. LiOH (0.24 g) was added slowly over a two hour period with stirring at ambient temperature. During this time, an initial yellow slurry changed into a clear, brown solution of the lithium salt. The methanol was removed and the residue brown oil dissolved with stirring over 24 hours in 50 ml DMF containing a 1.99 g of phenacyl bromide. A clear amber-colored solution was obtained. Two volumes of water were added and the mixture extracted with three 50 ml portions of ethylene dichloride. The organic extracts were combined and the volatile constituents removed in vacuo. The residue was dissolved in 50 ml of methanol and 1.16 g of maleic acid added, thus forming the maleate salt of phenacyl 1-isopropyl-9,10-dihydrolysergate formed in the above reaction. Addition of 150 ml of ether caused the maleate salt to precipitate as a nonohydrate; yield=2.31 g. The maleate salt was converted to the free base by dissolution in ethylene dichloride and washing the ethylene dichloride solution with 5% aqueous sodium bicarbonate. The free base was isolated by evaporation of the ethylene dichloride. The maleate salt was again formed in ether-methanol solution; yield=0.8 g of phenacyl 1-isopropyl-9,10-dihydrolysergate maleate monohydrate; mp=168°-170° C. Karl Fisher=2.94% water indicating monohydrate.

Analysis: Calc.: C, 65.90; H, 6.30; N, 4.90; Found: C, 65.61; H, 6.58; N, 4.73.

Other phenacyl esters preparable by the above procedure include:

p-Hydroxyphenacyl 1-isopropyl-9,10-dihydrolysergate maleate

Analysis: Calc.: C, 66.48; H, 5.84; N, 4.98; Found: C, 66.39; H, 5.91; N, 4.74.

p-Methoxyphenacyl 1-isopropyl-9,10-dihydrolysergate maleate

Analysis: Calc.: C, 66.65; H, 6.29; N, 4.86; Found: C, 66.39; H, 6.28; N, 4.65.

(±)-α-Methylphenacyl 1-isopropyl-9,10-dihydrolysergate maleate, mp=142°-145° C.

Analysis: Calc.: C, 68.56; H, 6.47; N, 5.36; Found: C, 68.83; H, 6.45; N, 4.87.

4-Phenylphenacyl 1-isopropyl-9,10-dihydrolysergate maleate

Mass spectrum: molecular ion (free base) at 506.

Analysis: Calc.: C, 78.57; H, 6.15; N, 4.56; Found: C, 78.82; H, 6.24; N, 4.64.

p-Chlorophenacyl 1-isopropyl-9,10-dihydrolysergate maleate

Analysis: Calc.: C, 64.19; H, 5.56; N, 4.89; Found: C, 63.93; H, 5.66; N, 4.95.

α,α-Dimethylphenacyl 1-isopropyl-9,10-dihydrolysergate maleate monohydrate

Mass spectrum: molecular ion (free base) at 458.

Analysis: Calc.: C, 66.89; H, 6.40; N, 4.70; Found: C, 67.01; H, 6.67; N, 4.74.

α-Methyl-p-hydroxyphenacyl 1-isopropyl-9,10-dihydrolysergate maleate

Analysis: Calc.: C, 66.65; H, 6.29; N, 4.86; Found: C, 66.39; H, 6.29; N, 5.15.

This invention also provides novel methods whereby 5HT receptors are blocked. Such methods are potentially useful in treating disease states in which an excess of circulating serotonin is a major contributing cause. These disease states include hypertension, anorexia nervosa, depression, mania, thrombosis, carcinoid syndrome, migraine and vasospasm. The compounds according to III above show relatively slight affinity for other receptors, $\alpha_1$, $\alpha_2$, $\beta$, histamine, carbachol etc. and thus are highly selective in their action. Formulations in which a compound of this invention is an active ingredient also form another aspect of this invention.

In order to demonstrate that compounds according to formula III have an extremely high affinity for $5HT_2$ receptors, apparent dissociation constants ($K_B$) as a measure of affinity for $5HT_2$ receptors, expressed as the negative logarithm, have been determined according to the following protocol.

Male Wistar rats (150-300 gram weight) were killed and their external jugular veins and thoracic aortas dissected free of connective tissue, cannulated in situ and placed in a modified Krebs' bicarbonate buffer in a suitable tissue bath. Two L-shaped 30-gauge stainless-steel hypodermic needles were inserted in each cannula and the dissected vessels gently pushed onto the needles. One needle was attached with thread to a stationary glass rod and the other to the transducer. [The procedure employed was that described by Hooker, Calkins and Fleisch, *Blood Vessels*, 14, 1, (1977) for use with circular smooth muscle preparations.]

The modified Krebs' bicarbonate buffer had the following makeup: (concentrations in millimoles): sodium chloride, 118.2; potassium chloride, 4.6; calcium chloride dihydrate, 1.6; potassium dihydrogenphosphate, 1.2; magnesium sulfate, 1.2; dextrose, 10.0; sodium bicarbonate, 24.8; and water q.s. to 1000 g. The tissue baths were maintained at 37° C. and were aerated with 95% oxygen-5% $CO_2$. An initial optimum resting force of 1 and 4 g was applied to the jugular veins and aorta, respectively. Isometric contractions were recorded as changes in grams of force on a Beckman Dynograph with Statham UC-3 transducers and microscale accessory attachment. Tissues were allowed to equilibrate 1 to 2 hours before exposure to drugs. Control responses to serotonin in the jugular vein and to norepinephrine in the aorta were obtained. The vessels were then incubated with appropriate concentrations of antagonist for one hour. Responses to serotonin or to norepinephrine were then repeated in the presence of the antagonist. Contraction to serotonin was evaluated in the jugular vein since this tissue produces marked responses to serotonin in the absence of alpha receptors—see Cohen and Wiley, *J. Pharm. Exp. Ther.*, 205, 400 (1978). Alpha receptor antagonist activity was evaluated in the aorta.

Apparent antagonist dissociation constants were determined for each concentration of antagonist according to the following equation:

$$K_B = \frac{[B]}{[\text{dose ratio} - 1]}$$

wherein [B] is the concentration of the antagonist and the dose ratio is the $ED_{50}$ of the agonist in the presence of the antagonist divided by the control $ED_{50}$. These results are then expressed as the negative logarithm of $K_B$. The $-\log K_B$ values obtained for compounds of this invention are given below in Table 1.

TABLE 1

Apparent Dissociation Constants for $5HT_2$ receptors determined in the rat jugular vein.

| Compound | | | | $5HT_2$ |
|---|---|---|---|---|
| $R^3$ | $R^4$ | $R^{10}$ | salt | $-\log K_b \pm$ S.E. |
| H | H | H | maleate.$H_2O$ | 7.82 ± .09 |
| $CH_3$ | H | H | maleate | 8.34 ± .17 |
| H | H | p-$OCH_3$ | maleate | 8.89 ± .07 |
| $CH_3$ | H | p-OH | maleate | 9.46 ± .13 |
| H | H | p-Cl | maleate | 7.46 ± .12 |
| H | H | p-phenyl | maleate | 7.15 ± .30 |
| $CH_3$ | $CH_3$ | H | maleate | 7.83 ± .15 |
| H | H | p-OH | maleate.$H_2O$ | 9.86 ± .11 |

In mammals, hypertension may be mediated through $5HT_2$ receptors. Thus, compounds of formula III would be expected to lower blood pressure in humans as does ketanserin, another 5HT₂ blocker, but without the side effects attributable to alpha adrenergic receptor blockade of ketanserin.

In carrying out our novel therapeutic process, a pharmaceutically-acceptable salt of a drug according to formula III above formed with a non-toxic acid is administered orally or parenterally to a mammal with an excess of circulatory serotonin in which mammal it is desirable to block 5HT₂ receptors in order to alleviate symptoms attributable to excessive serotonin levels such as high blood pressure and migraine. For parenteral administration, a water soluble salt of the drug is dissolved in an isotonic salt solution and administered by the i.v. route. For oral administration, a pharmaceutically-acceptable salt of the drug is mixed with standard pharmaceutical excipients such as starch and loaded into capsules or made into tablets, each containing 0.1 to 100 mg of active drug. Dosage levels of from 0.1–10 mg/kg have been found to be effective in blocking 5HT₂ receptors. Thus, the oral dosage would be administered 2–4 times per day, giving a daily dosage range of about 0.003 to about 10.0 mg./kg. per day.

Other oral dosage forms, suspensions, elixirs and tablets, can also be utilized and are preparable by standard procedures.

We claim:

1. A compound of the formula:

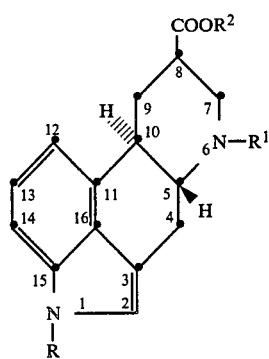

wherein R is primary or secondary $C_{1-8}$ alkyl, $C_{2-4}$ alkenyl-$CH_2$, $C_{3-8}$ cycloalkyl or $C_{3-6}$ cycloalkyl substituted $C_{1-5}$ primary or secondary alkyl, the total number of carbon atoms in R not to exceed 8; $R^1$ is allyl, H or $C_{1-4}$ straight-chain alkyl; and $R^2$ is

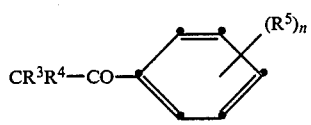

wherein $R^3$ and $R^4$ can be individually H, $CH_3$ or $C_2H_5$; n can be 0, 1 or 2; $R^5$ can be OH, $OC_{1-3}$ alkyl, chloro, bromo, fluoro, $CH_3$, $CF_3$ or $C_2H_5$ when n is 1 or 2; $R^5$ can be phenyl when n is 1; and when n is 2 the adjacent $R^5$ substituents can be taken together to form a methylenedioxy substituent.

2. A compound according to claim 1 in which R is isopropyl.

3. A compound according to claim 1 in which $R^1$ is H.

4. A compound according to claim 1 in which $R^1$ is $C_{1-4}$ straight chain alkyl.

5. A compound according to claim 1 in which $R^2$ is phenacyl.

6. A compound according to claim 1 in which $R^2$ is p-hydroxyphenacyl.

7. A compound according to claim 1, said compound being p-hydroxyphenacyl 1-isopropyl-9,10-dihydrolysergate.

8. A compound according to claim 1, said compound being α-methyl-p-hydroxyphenacyl 1-isopropyl-9,10-dihydrolysergate.

9. A compound according to claim 1, said compound being α-methylphenacyl 1-isopropyl-9,10-dihydrolysergate.

10. A compound according to claim 1, said compound being p-methoxyphenacyl 1-isopropyl-9,10-dihydrolysergate.

11. A method of blocking 5HT₂ receptors which comprises administering to a mammal having an excess of serotonin centrally or peripherally an 5HT₂ blocking dose of a compound according to claim 2.

12. A method of treating hypertension which comprises administering to a hypertensive mammal, a hypotensive dose of a compound according to claim 2.

13. A method of treating migraine which comprises administering to a mammal suffering from migraine, a migraine relieving dose of a compound according to claim 2.

14. A method of treating vasospasm which comprises administering to a mammal experiencing vasospasm, a vasospasm relieving dose of a compound according to claim 2.

15. A process according to claim 11 in which p-hydroxyphenacyl 1-isopropyl-9,10-dihydrolysergate is the drug employed.

16. A process according to claim 11 in which α-methyl-p-hydroxyphenacyl 1-isopropyl-9,10-dihydrolysergate is the drug employed.

17. A process according to claim 11 in which α-methylphenacyl 1-isopropyl-9,10-dihydrolysergate is the drug employed.

18. A process according to claim 11 in which p-methoxyphenacyl 1-isopropyl-9,10-dihydrolysergate is the drug employed.

* * * * *